United States Patent [19]

Roberts

[11] Patent Number: 4,938,409
[45] Date of Patent: Jul. 3, 1990

[54] BRAZED POROUS COATING AND IMPROVED METHOD OF JOINING METAL WITH SILVER MATERIAL

[75] Inventor: Peter R. Roberts, Groton, Mass.
[73] Assignee: Nuclear Metals, Inc., Concord, Mass.
[21] Appl. No.: 297,118
[22] Filed: Jan. 17, 1989

Related U.S. Application Data

[62] Division of Ser. No. 162,072, Feb. 29, 1988, Pat. No. 4,813,965.

[51] Int. Cl.$^5$ ................................................ A61F 1/24
[52] U.S. Cl. ................................................... 228/178
[58] Field of Search ............... 228/178, 193, 120, 121, 228/122, 183, 221, 263.18; 29/163.8; 427/2, 205; 623/23, 22

[56] References Cited

U.S. PATENT DOCUMENTS

| | | | |
|---|---|---|---|
| 3,647,498 | 3/1972 | Dougherty | 427/2 |
| 3,751,283 | 8/1973 | Dawson | 228/122 |
| 3,973,718 | 8/1976 | Deschamps | 228/183 |
| 4,644,942 | 2/1987 | Sump | 427/2 |
| 4,661,071 | 4/1987 | Bell et al. | 427/2 |
| 4,749,594 | 6/1988 | Malikowski et al. | 427/205 |
| 4,854,496 | 8/1989 | Bugle | 228/193 |

Primary Examiner—M. Jordan
Attorney, Agent, or Firm—Joseph S. Iandiorio

[57] ABSTRACT

Pieces of metal are joined with silver material in a two-stage heating process. In one application, a brazed porous coating of metal particles on a metal substrate of a device is formed by interposing a silver material between the substrate and the particles, and placing the particles onto the substrate. The device is heated to a first temperature slightly below the melting point of the silver material, then briefly heated to a second temperature above 1100° C. to rapidly melt the silver material to wet the particles and substrate and to generate alloying among the silver material, the particles, and the substrate. The device is allowed to cool to solidify the alloy and unite the particles and substrate to form a porous coating on the device. Also disclosed are a prosthetic device having a metal shaft for insertion into a bone canal, and a porous coating of metal particles brazed to the metal shaft by a silver material. A porous coating preparation to be applied to a metal substrate, including metal particles, silver material, and a vaporizable binder for initially securing the particles to the substrate is further disclosed.

25 Claims, 2 Drawing Sheets

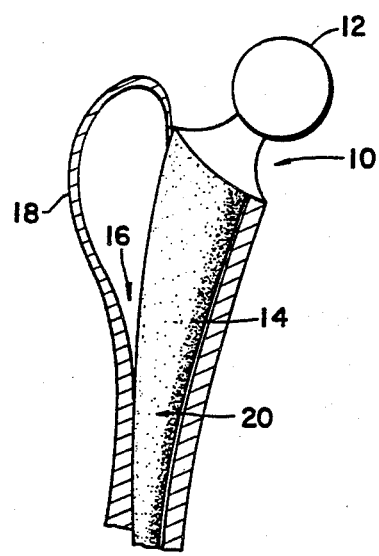
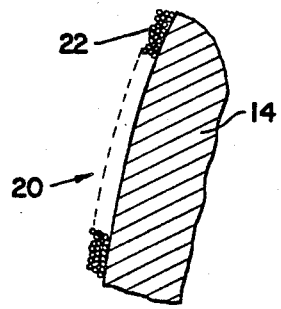
Fig. 1A    Fig. 1B
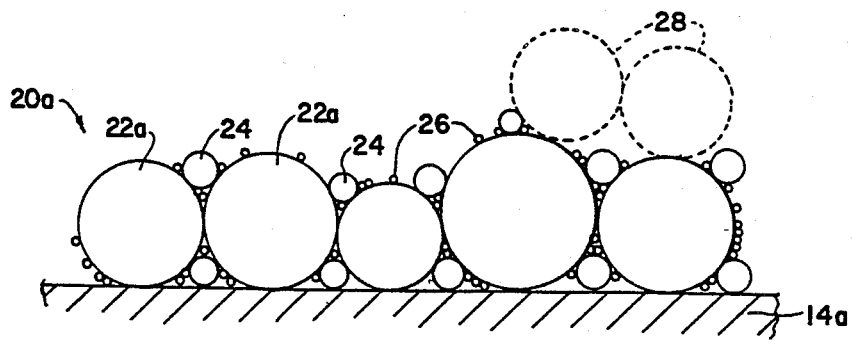
Fig. 2
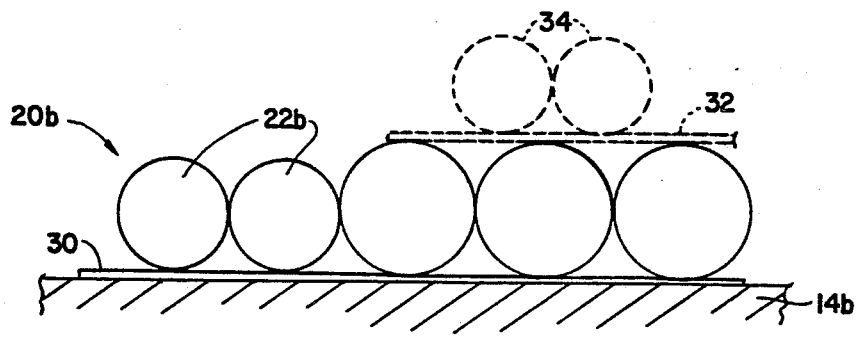
Fig. 3

BRAZED POROUS COATING AND IMPROVED METHOD OF JOINING METAL WITH SILVER MATERIAL

This is a division of application Ser. No. 162,072, filed Feb. 29, 1988 now U.S. Pat. No. 4,813,965 issued 3/21/89.

FIELD OF INVENTION

This invention relates to the joining of metal pieces with silver material through an alloying process and more particularly to an improved porous coating for a metal substrate such as a prothesis device which includes silver utilized as a brazing medium to secure the particles to the substrate while minimizing transformation of the grain microstructure of the substrate.

BACKGROUND OF INVENTION

There are a number of applications in which metal or metal alloy paritcles must be bonded together and to a metal substrate. An effective method for joining the particles involves sintering, that is, heating without melting the particles, to bond the particles by diffusion of their constituent material. The diffusion bonding forms "necks" which join the particles to themselves and to a metal substrate. Sintering presently requires moderate to high heating of the particles in a vacuum or inert atmosphere for a long period of time. However, the lengthy treatment at a sufficiently high temperature begins to degrade the metal substrate through transformation of its grain microstructure. The substrate begins to exhibit decreased fatigue crack initiation resistance and other weaknesses.

One application of sintered particles involves formation of porous coating for prosthetic devices. There is a large and increasing demand for prosthetic devices such as replacement joints. Serious arthritic problems, for example, are often alleviated through surgery involving implantation of a metal joint into the bone of the patient to replace the natural joint. The metal joint is held by a shaft which was often anchored into the bone using an acrylic bone cement such as a grout. However, patients receiving such surgery are becoming younder in age and are living longer and more active lives. The bone cement used to anchor the shaft may not be sufficiently durable.

To improve adhesive performance and in certain instances to avoid the use of bone cement, one construction of prosthetic devices utilizes a coarse powder sintered onto a shaft made from a strong alloy such as Ti-6Al-4V alloy or cobalt alloy. In the latter case the resultant porous coating enables the living bone surrounding the shaft to grow into the pores and firmly lock the prosthesis in place. The powder may be of the same composition as the metal substrate, e.g. Ti6Al4V alloy or cobalt alloy having a composition as defined by the specification ASTM F-75; pure titanium powder (CpTi) is also used to coat titanium alloy prosthesis stems. The particles are initially secured to the substrate using an organic binder, which volatilizes below the sintering temperature. For sintering to Ti6Al4V, particles and binder are placed in a furnace at 1250° C. for three hours in a high vacuum, e.g., $10^{-6}$ mm Hg. However, the Ti6Al4V alloy undergoes a solid state phase transformation at temperatures above 1000° C. The microstructure is transformed to a form which lowers fatigue resistance. In addition, the diffusion bonds developed in the standard sintering process tend to have small areas of contact, that is, there are small radii of curvature of the fillet formed in the "notch" or neck region between particle and substrate. These bonds thus may be inherently weak; if the hard vacuum is not maintained the bond may be weakened further by embrittlement due to contamination by oxygen and nitrogen (air), and by carbon from back-streamed oil vapor from the pumping system. These weaknesses may cause the prosthesis to fail after implantation in a patient.

SUMMARY OF INVENTION

It is therefore an object of this invention to provide an improved method for joining pieces of metal while minimizing degradation of metal.

It is a further object of this invention to provide an improved porous coating amd method of making same for a metal substrate such as the shaft of a prosthetic device.

It is a further object of this invention to provide such a coating which is formed while minimizing transformation of the grain microstructure of the substrate.

It is a further object of this invention to provide an improved prosthetic device having a shaft with increased fatigue resistance.

A still further object of this invention is to provide an improved method of bonding particles to a substrate in a period of time shorter than that required for sintering.

It is a further object of this invention to provide such a method which can provide stronger attachment of the particles.

Yet another object of this invention is to provide a novel preparation for forming a porous coating on a metal substrate.

It is a further object of this invention to provide improved bonding of particles to a substrate characterized by larger radii of curvature at the particle-substrate neck region while still retaining a desired porosity.

This invention results from the realization that truly effective bonding of metal pieces such as metal particles and the metal shaft of a prosthetic device may be achieved by inserting or otherwise introducing silver between the particles and the shaft, heating the elements at a first temperature, and briefly heating the elements at a higher temperature to melt the silver to wet the particles and the shaft and generate alloying among the elements to form a metal-silver alloy extending into the particles and the shaft.

This invention features a method of forming a brazed porous coating of metal particles on a metal substrate of a device, including interposing a sliver material between the substrate and the particles, and placing the particles onto the substrate. The method further includes heating the device to a first temperature slightly below the melting point of the silver material, and briefly heating the device to a second temperature above 1100° C. to rapidly melt silver material to wet the particles and substrate and to generate alloying among the silver material, the particles, and the substrate. The device is allowed to cool to solidify the alloy and unite the particles and substrate to form a porous coating on the device. Also featured is a device formed by this method.

In one embodiment, interposing includes coating the praticles, the substrate, or both with the silver material. The coating may include applying a mixture of the silver material and a vaporizable binder for initially securing the particles to the substrate. Alternatively, interposing includes placing the silver material as a foil between the particles and the substrate.

In another embodiment, the first temperature ranges from 850° to 955° C., preferably approximately 950° C., and the device is heated for at least 5 minutes at the first temperature. The second temperature ranges from 1150° to 1260° C., preferably approximately 1250° C., for 10 to 30 min.

The silver material may be substantially pure silver or an alloy of silver and at least one additional biologically inert element, such as gold. The device may be prosthetic device, having as a major constituent titanium or cobalt. The particles may range in size from 0.175 mm to 1 mm and may be generally spherical.

This invention also features a prosthetic device including a metal shaft for insertion into a bone canal, and a porous coating of metal particles brazed to the metal shaft by a silver material.

This invention further features a porous coating preparation to be applied to a metal substrate, including metal particles, silver material, and a vaporizable binder for initially securing the particles to the substrate.

DISCLOSURE OF PREFERRED EMBODIMENT

Other objects, features and advantages will occur from the following description of a preferred embodiment and the accompanying drawings, in which:

FIG. 1A is an elevational cross-sectional view of a terminal portion of a bone with a prosthetic device according to this invention inserted into it;

FIG. 1B is an enlarged partial elevational view of the porous coating of the device of FIG. 1A;

FIG. 2 is an enlarged schematic elevational view of particles coated with silver and an organic binder which attaches the particles to the substrate before heating;

FIG. 3 is a schematic elevational view of an alternative arrangement of the silver as a foil;

Figure 4:
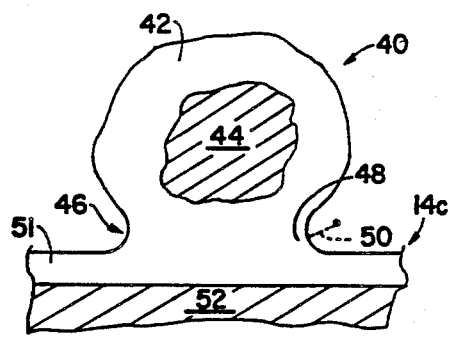
FIGS. 4 and 5 are cross-sectional views of a particle bonded to a substrate after brief heating to 1100° and 1250° C., respectively.

This invention may be accomplished by the bonding of metal pieces such as metal particles and a metal substrate such as the shaft of a prosthetic device by interposing a silver material between the particles and the substrate. A method of bonding according to this invention involves heating the device to a first temperature slightly below melting point of the silver material, and briefly heating the device to a second temperature above 1100° C. to rapidly melt the silver material. The melted silver material wets the particles and substrate and, because of the high temperature, preferential grain attack of the particles and substrate by the silver material is minimized. An alloy of the silver material and the metal piece is generated which, upon cooling, firmly bonds the metal pieces.

The use of two different temperatures accomplishes several important results. Although pure silver melts at 960° C., it was found that liquid silver exhibits grain boundary penetration between temperatures ranging approximately from 980° to 1050° C. Preheating the silver at the first temperature, e.g. 950° C., such as in a first zone of a two-zone furnace, enables quick transition to a higher temperature by moving the device to the second, hotter zone of the furnace. The brief period of time at the second temperature is important because metal substrates such as Ti-6Al-4V alloy, ASTM F136-79 specification, exhibit time-dependent beta transus of its grain microstructure at temperatures above approximately 1000° C. (1825° F.).

The silver material may be pure silver or may be an alloy of silver in combination with one or more other biologically inert ingredients. While silver is used in conventional hard solders or brazing materials, it is frequently alloyed with toxic elements such as cadmium or nickel. These commerical alloys are unsuitable for body implant use. Preferably, the biologically inert material combined with silver according to the present invention depresses the melting point of the alloy below 960° C. to further minimize beta transus of the metal substrate. For example, ten weight percent tin depresses the melting point of silver from 960° C. to 880° C. Further, the tim may lower the corrosiveness of the silver during the liquid phase. However, as described below, the silver material can have a melting point nearly as high as 1100° C. while still permitting brazing during the brief heating of the deivce above 1100° C. For example, pure gold has a melting point of 1063° C.; an alloy of 75% silver and 25% gold has a melting point of approximately 1000° to 1010° C., still well below 1100° C. The term silver material hereinafter refers to either a biologically inert alloy of silver or to substantially pure silver.

A prosthetic device according to this invention carries a porous coating of metal particles brazed to the metal shaft of the device by a silver material. Prosthetic device 10, FIG. 1A, includes ball joint 12 attached to stem 14 which is shown inserted within bone canal 16 of femur 18. Stem 14 retains its original strength and resistance to fatigue due to porous coating 20 according to this invention which, during its formation, enables minimum exposure to temperatures above the beta transus temperature of stem 14.

Porous coating 20 is shown in greater detail in FIG. 1B as a layer one to three particles thick on stem 14. Particles 22 are held in place by silver material.

The silver material may be interposed between the particles and the substrate using several techniques. A porous coating composition of particles, flaked or particulate silver material, and a conventional organic binder can be painted onto the substrate to form porous coating 20a, FIG. 2. Porous coating 20a, shown before heating, includes particles 22a having a diameter of 0.175 to 1 mm. Particles 22a are generally spherical, such as −60+80 mesh P.R.E.P. CpTi grade II powder, available from Nuclear Metals, Incorporated, Concord, Massachusetts. Silver material 24, e.g., a fine silver powder of 1 μm −10 μm, is mixed with organic binder that will hold the particles in place and then volatilize without trace and without affecting the metallic components chemically or disrupting the structure. Organic binders typically include polyvinyl alcohol, polyethylene or polystyrene, which coat particles 22a and silver material 24 as a film 26. During heating, organic binder film 26 vaporizes without leaving a residue. Phantom particles 28 indicate that porous coating 20a can be formed several particle layers in thickness.

Alternatively, the silver is deposited through physical vapor deposition upon the substrate, the paticles, or both, or is placed as a foil between the particles and the substrate, such as shown for foil 30 between particles 22b and substrate 14b, FIG. 3. Again, porous coating 20b can be several particles in thickness as indicated by additional foil 32 and particles 34, shown in phantom.

After the silver material and particles are placed on the substrate, the device is heated in two stages. The device is heated to a first temperature slightly below the melting point of the silver material until the metal is heated to that temperature. When the silver material is substantially pure silver, having a melting point of 960° C., the device can be heated to 950° C. for at least 30 minutes, preferably 30 to 60 minutes. The device is then briefly heated, such as by moving it into the hotter zone of a two-zone furnace, to a second temperature above 1100° C. to rapidly melt the silver material to wet the particles and substrate. A bulk reaction is preferably achieved, without preferential intergranular attach of the particles and substrate by the silver material. It is desirable to maintain the device above the beta transus temperature of the substrate for as short a time as possible to avoid disadvantageous transformation of its grain microstructure. Because transformation is time dependent, brief heating above the transus temperature minimizes the effect on the alloy.

The heating may be accomplished in a vacuum or in an atmosphere of an inert gas. For example, the device can be heated in an atmosphere of helium at 3 psi above atmospheric pressure.

During heating at the second temperature, the silver melts and wets the surface of the particles and the substrate. When the second temperature used with pure silver is at least 1250° C. the microstructure becomes single phase with even distribution of alloyed silver across spherical particle and an increase at the original boundary. After cooling, a fillet is formed which secures particles to the substrate. Similarly, fillets are formed between particles to further secure the particles to each other and to the substrate.

Several experiments were conducted using aluminum and silver as solder materials. The aluminum brazed material produced inferior bonding strengths. Temperatures as high as 1375° C. were employed to promote maintenance of a liquid phase to obtain brazing connection, but the results were not successful. In contrast, silver as the brazing material produced bonds as strong as or stronger than bonds achieved by conventional sintering, even during a realtively short exposure time of 10 minutes at temperatures above 1100° C. By comparison, conventional sintering treatments involve a three-hour exposure at 1250° C. The metal substrates for the experiments involving the aluminum and silver coating were cylinders of Ti-6Al-4V alloy, 0.7 inch in diameter and 0.5 inch in height. One face of each cylinder was grounded to number 600 grit with SiC disks and coated through physical vapor deposition to thicknesses of 4–10 μm of aluminum and 2–35 μm silver. A monolayer of CpTi grade II powder was glued to the coated cylinders using an organic binder. Aluminum has a melting point of 660° C., the aluminum coated specimens were heated to 650° C. for 15–30 minutes, moderately heated to 660° C., and then rapidly heated to temperatures ranging from 670° C. to 1375° C. as shown in Table I:

TABLE I

| TREATMENTS WITH Al COATINGS | | | | | | | |
|---|---|---|---|---|---|---|---|
| step | 1 | 2 | 3 | 4 | 5 | 6 | 7 |

A - 670° C., Vacuum $10^{-6}$ torr, He Quench in final segment

TABLE I-continued

| TREATMENTS WITH Al COATINGS | | | | | | | |
|---|---|---|---|---|---|---|---|
| step | 1 | 2 | 3 | 4 | 5 | 6 | 7 |
| t | 30 min | 30 min | 60 sec | 10 sec | — | — | — |
| T °C. | 621 | 650 | 670 | 0 | — | — | — |
| B - 670° C., Vacuum $10^{-6}$ torr, He Quench in final segment — | | | | | | | |
| t | 30 min | 30 min | 60 sec | 300 sec | 10 sec | — | — |
| T °C. | 621 | 650 | 660 | 670 | 0 | — | — |
| C - 1050° C., Vacuum $10^{-6}$ torr, Furnace cool in final segment | | | | | | | |
| t | 20 min | 15 min | 1h | 15 min | 15 min | 1h | 10s |
| T °C. | 650 | 670 | 670 | 1010 | 1050 | 1050 | 0 |
| D - 1375° C., Vacuum $10^{-6}$ torr, Furnace cool in final segment | | | | | | | |
| t | 5 min | 15 min | 50 sec | 30 sec | 30 min | 30 min | 10s |
| T °C. | 40 | 650 | 675 | 675 | 1375 | 1375 | 0 |

All heat treatments for aluminum coating were in a vacuum of $10^{-6}$ torr.

The silver coated specimens were heat treated either in the high vacuum or in an ultra-high purity helium atmosphere at 3 psi above atmospheric pressure. The treatment period is shown below in Table II:

TABLE II

| TREATMENTS WITH Ag COATINGS | | | | | | |
|---|---|---|---|---|---|---|
| step | 1 | 2 | 3 | 4 | 5 | 6 |
| time | 5 min | 20 min | 5 min | 5 min | 10 min | 10 s |
| Temp. °C. | 45 | 950 | 950 | X | X | 0 | where X=980, 1050, 1065, 1100, 1150, 1200, or 1250° C. In addition to the ten-minute heat treatment time during segment 5, twenty-minute heating periods were also provided at 1050 and 1150° C. The devices were within furnace cooled for 100 to 150 minutes down to 950° C.

After examining the specimens it was determined that most of the silver was lost through vaporization when the specimen was heated in a vacuum enviroment. Loss through vaporization of silver in the helium environment was minimal.

The bonding strength of the particles was mechanically tested relative to a control which received a three-hour sintering treatment at 1250° C. The treatments below 1100° C. exhibited inferior bonding strength while heat treatments at or above 1100° C. exhibited slightly improved bonding strength over the control. Increasing the heat treatment during segment 5 from ten to twenty minutes did not significantly improve bonding strength. However, a clearly superior bond strength was obtained by treatment at 1250° C. Thus, bonding strengths equal to or greater than that provided by eventual sintering were achieved by heating the specimen above the beta transus temperature for as little as ten minutes to the temperatures ranging from 1100° to 1250° C. In contrast, conventional sintering treatment requires heating at 1250° C. for a period of 18 times longer, that is, for three hours.

Figure 5:
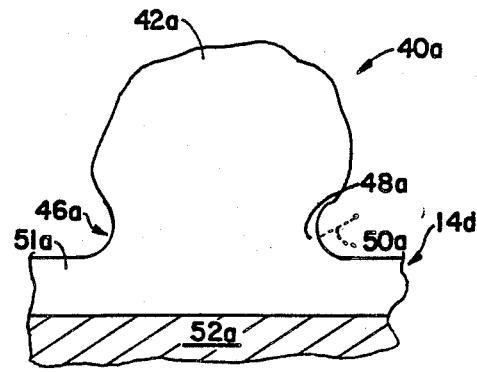

A cross-sectional view of a particle and substrate bonded for ten minutes at 1100° and 1250° C. are shown in FIGS. 4 and 5, respectively. Particle 40, FIG. 4, exhibits a silver-rich alloy layer 42 which penetrates to a depth of approximately one-half of the radius of particle 40. Core 44 substantially retains its original titanium alloy composition. Particle 40 is bonded to substrate 14c at neck region 46 by fillet 48. Fillet 48 exhibits a large radius of curvature indicated by dashed line 50. Alloy 42 continues through neck region 46 and penetrates substrate 14c as shown by alloy layer 51 lying above original material 52.

Treatment for ten minutes at 1250° C. produced silver-rich alloy 42a which is distributed fairly evenly throughout particle 40a. Fillet 48a of neck region 46a exhibited a larger radius of curvature 50a. Similarly, silver-rich alloy 51a penetrated more deeply into substrate 14d.

Figure 6A:
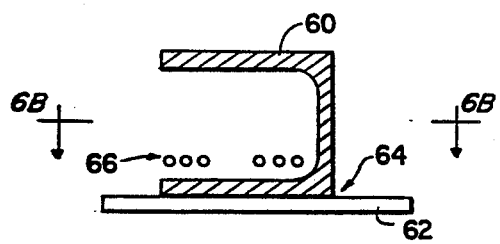
FIG. 6A is a cross-sectional end elevational view of the bonding of a beam and a substrate according to this invention.
Figure 6B:
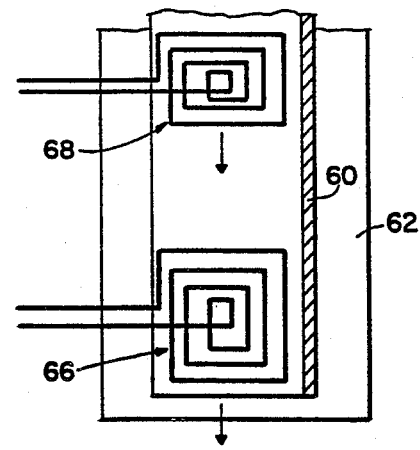
FIG. 6B is a top elevational view along lines 6B—6B of FIG. 6A showing two travelling heating coils which accomplish heating to the first and second temperatures according to this invention.

While the process of bonding with silver material is described above in relation to the bonding of particles to a substrate, this is not a limitation on the invention. Beam 60, FIG. 6A, is shown in cross section during bonding to substrate 62. Silver material 64 is interposed between beam 60 and substrate 62, and heating coil 66 is passed over the area to accomplish bonding according to this invention. A top partial cross-sectional view along lines 6B—6B is shown in FIG. 6B with the first temperature being applied by preheat coil 66 and the second temperature provided by second heating coil 68. Preheat coil 66 is more elongated than second coil 68 so that, when coils 66, 68 travel at the same rate, beam 60 and substrate 62 are subjected to the first temperature for a longer period of time. Alternatively, beam 60, sheet 62 and material 64 are passed through an elongated furnace at 950° C. and then briefly through a smaller furnace at 1250° C.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. A method of forming a brazed porous coating of metal particles on a metal substrate of a device, comprising:
    interposing a silver material between the substrate and the particles, and placing the particles onto the substrate;
    heating the device to a first temperature slightly below the melting point of the silver material;
    briefly heating the device to a second temperature above 1100° C. to rapidly melt the silver material to wet the particles and substrate and to generate alloying among the silver material, the particles, and the substrate; and
    allowing the device to cool to solidify the alloy and unite the particles and substrate to form a porous coating on the device.

2. The method of claim 1 in which interposing includes coating the particles, the substrate, or both with the silver material.

3. The method of claim 2 in which coating includes applying a mixture of the silver material and a vaporizable binder for initially securing the particles to the substrate.

4. The method of claim 1 which interposing includes placing the silver material as a foil between the particles and the substrate.

5. The method of claim 1 in which the first temperature ranges from 850° to 955° C.

6. The method of claim 5 in which the device is heated for at least 5 min at the first temperature.

7. The method of claim 1 in which the silver material is substantially pure silver and the first temperature is approximately 950° C.

8. The method of claim 1 in which the second temperature ranges from 1150° to 1260° C.

9. the method of claim 8 in which the device is heated fro 10 to 30 min at the second temperature.

10. The method of claim 1 in which the second temperature is approximately 1250° C.

11. The method of claim 1 further including surrounding the device in an atmosphere consisting substantially of helium.

12. The method of claim 1 in which the silver material is substantially pure silver.

13. The method of claim 1 in which the silver material is an alloy of silver and at least one additional biologically inert element.

14. The method of claim 13 in which the inert element is substantially pure gold.

15. The method of claim 1 in which the device is a prosthetic device.

16. The method of claim 15 in which a major constituent of the particles and the substrate is titanium or cobalt.

17. The method of claim 1 in which the particles range in size from 0.175 mm to 1 mm.

18. The method of claim 1 in which the particles are generally spherical.

19. The device formed by the method of claim 1.

20. A method of forming a brazed porous coating of metal particles on a metal substrate of a device, comprising:
    interposing a silver material between the substrate and the particles, and placing the particles onto the substrate;
    heating the device to a first temperature slightly below the melting point of the silver material for at least 5 min;
    briefly heating the device to a second temperature above 1100° C. for 10 to 15 min to rapidly melt the silver material to wet the particles and substrate and to generate alloying among the silver material, the paritcles, and the substrate; and
    allowing the device to cool to solidify the alloy and unite the particles and substrate to form a porous coating on the device.

21. A method of joining at least two pieces of metal, comprising:
    interposing a silver material between the metal pieces, and placing the metal pieces together;
    heating the metal pieces to a first temperature slightly below the melting point of the silver material;
    briefly heating the metal piece to a second temperature above 1100° C. to rapidly melt the silver material to wet the metal pieces and to generate alloying among the silver material and the metal pieces; and
    allowing the metal pieces to cool to solidify the alloy and unite the metal pieces.

22. A porous coating preparation to be applied to a metal substrate, comprising metal particles, silver material, and a vaporizable binder for initially securing said particles to the substrate.

23. The preparation of claim 22 in which the silver material is substantially pure silver.

24. The preparation of claim 23 in which the silver material is an alloy of silver and at least one additional biologically inert element.

25. The preparation of claim 22 in which the particles range is size from 0.175 mm to 1 mm.

* * * * *